United States Patent [19]

Nicholson et al.

[11] 4,312,361
[45] Jan. 26, 1982

[54] PRESSURE MONITORING SYSTEM FOR ELECTROFLUIDIC SENSING DEVICES

[75] Inventors: James E. Nicholson, Lincoln; Lawrence Milesky, Needham, both of Mass.

[73] Assignee: Codman and Shurtleff, Inc., Randolph, Mass.

[21] Appl. No.: 31,705

[22] Filed: Apr. 20, 1979

[51] Int. Cl.³ .............................................. A61B 5/00
[52] U.S. Cl. ...................................... 128/748; 73/723; 73/731
[58] Field of Search .............................. 128/680–683, 128/748; 73/700–701, 709, 712, 715, 723, 729, 731, 753

[56] References Cited

U.S. PATENT DOCUMENTS

| | | | |
|---|---|---|---|
| 3,104,661 | 9/1963 | Holpern | 128/683 |
| 3,452,744 | 7/1969 | Van Deu Nieuwenhof et al. | 128/683 |
| 3,636,941 | 1/1972 | Guerrekian | 128/683 |
| 3,649,948 | 3/1972 | Porter | 339/16 R |
| 3,744,490 | 7/1973 | Fernrandez | 128/683 |
| 3,789,667 | 2/1974 | Porter et al. | 73/731 |
| 4,050,452 | 9/1977 | Lee | 128/683 |
| 4,058,117 | 11/1977 | Kaspari et al. | 128/682 |
| 4,080,653 | 3/1978 | Barnes, Jr. et al. | 128/748 |
| 4,147,161 | 4/1979 | Ikebe et al. | 73/731 |

*Primary Examiner*—Robert W. Michell
*Assistant Examiner*—Francis J. Jaworski
*Attorney, Agent, or Firm*—Donal B. Tobin

[57] ABSTRACT

A pressure monitoring system for use with an electrofluidic device for sensing pressure includes a pump for supplying fluid to the electrofluidic sensing device. An electrical switching circuit controls the supply of fluid to the sensing device and is responsive to the external pressure level applied to the sensing device; this circuit also cyclically causes the supplied pressure to vent when the pressure of supplied fluid inside the sensing device is substantially equal to the applied external pressure, and then start the fluid supply to the device over again. This system further includes a measuring element for detecting the pressure level of the supplied fluid, and a digital meter for displaying the analogous detected pressure level during supply of the fluid.

16 Claims, 9 Drawing Figures

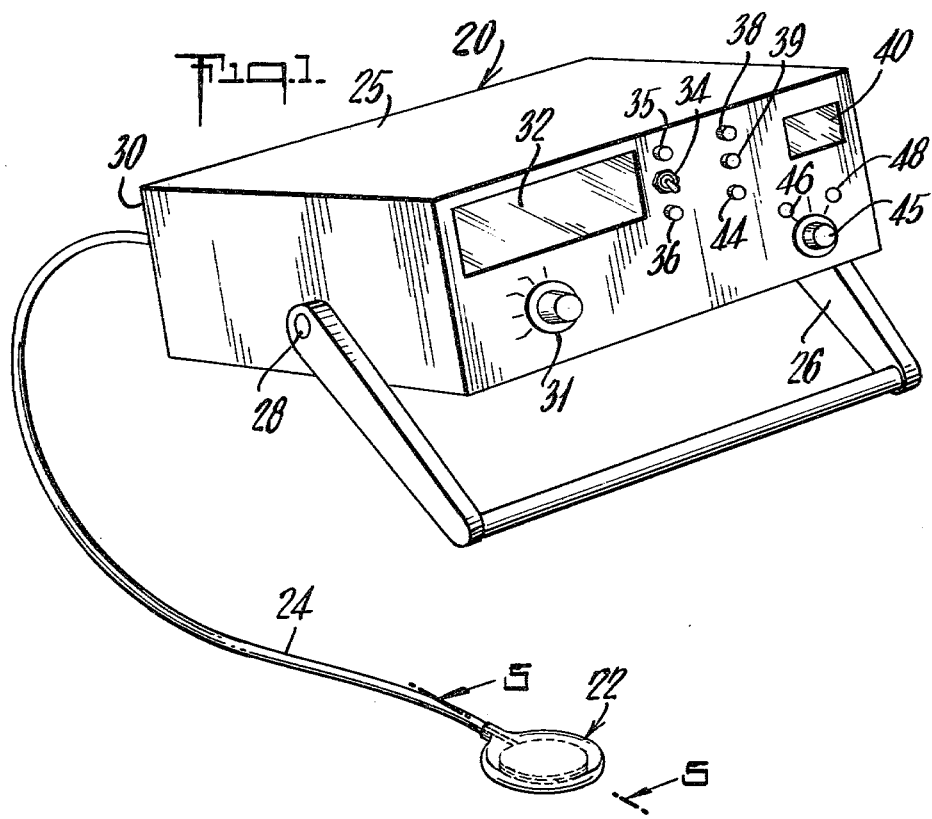
Fig. 1.
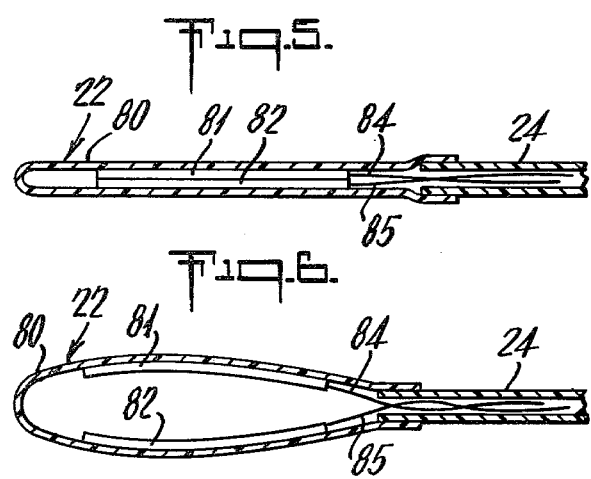
Fig. 5.
Fig. 6.

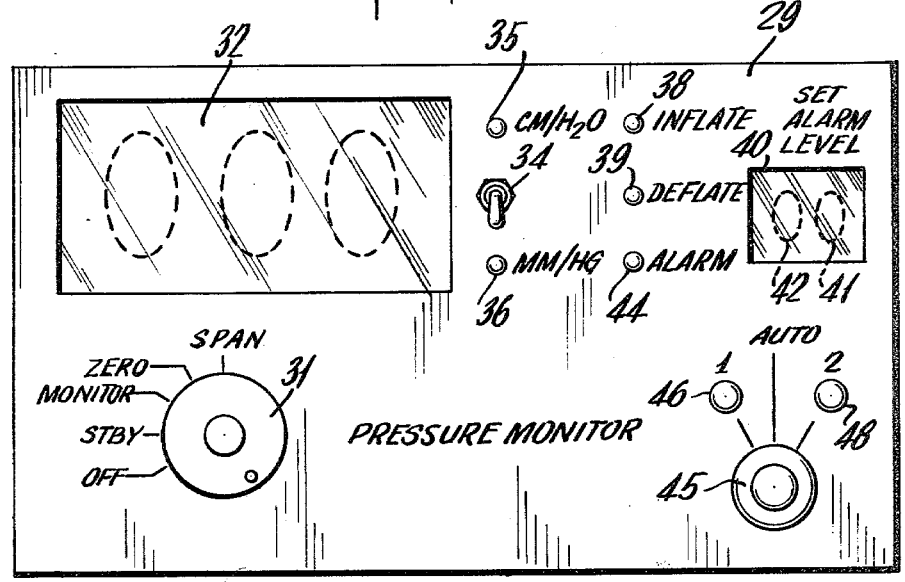
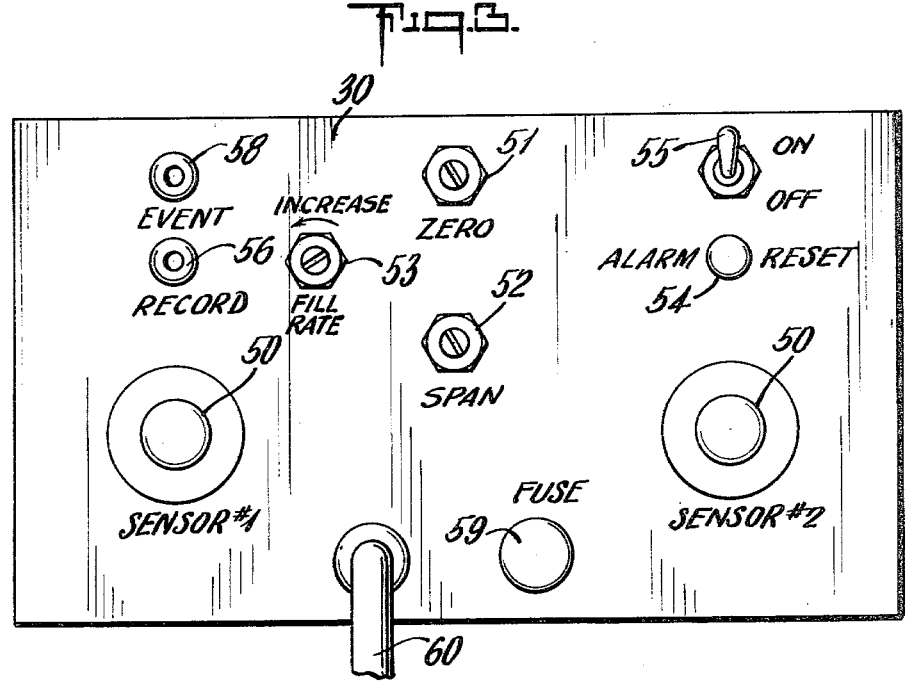

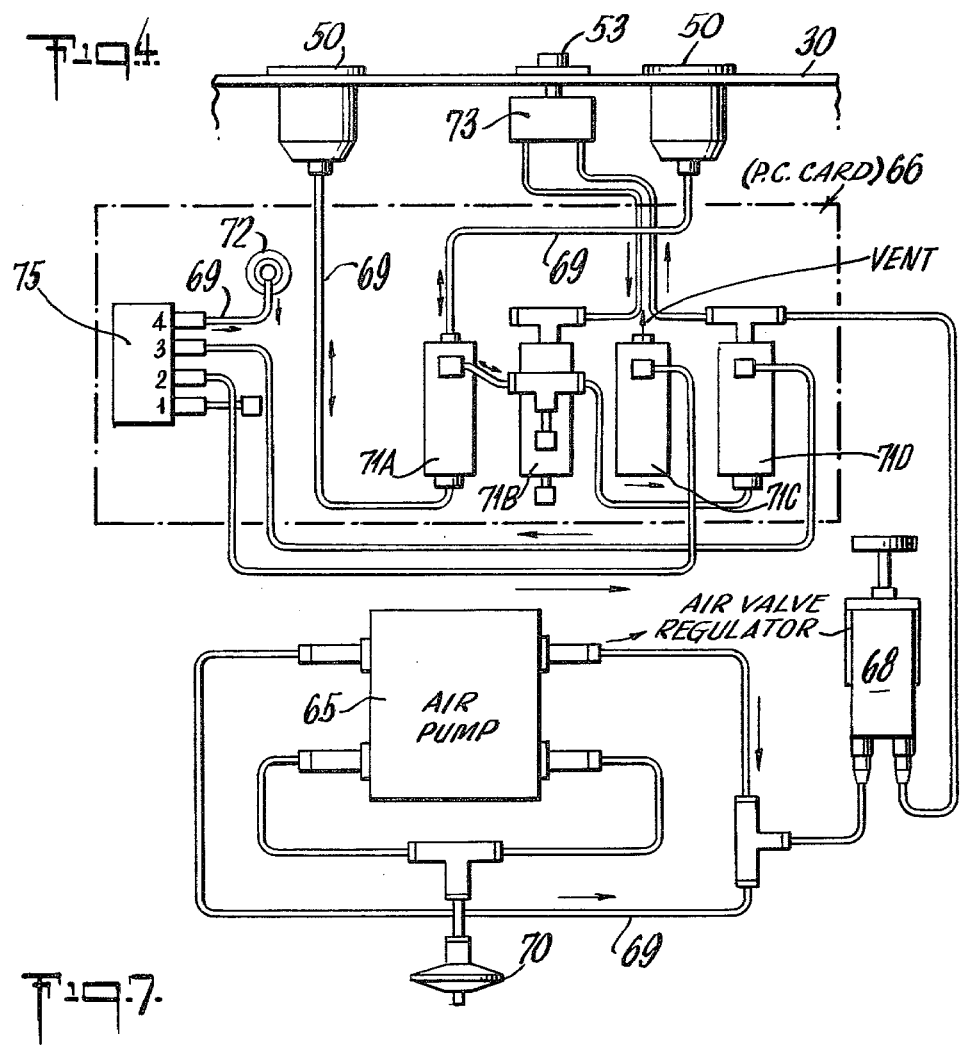
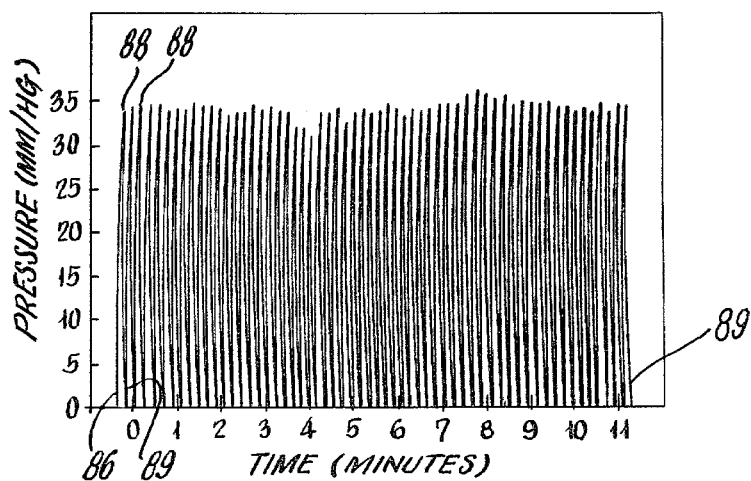

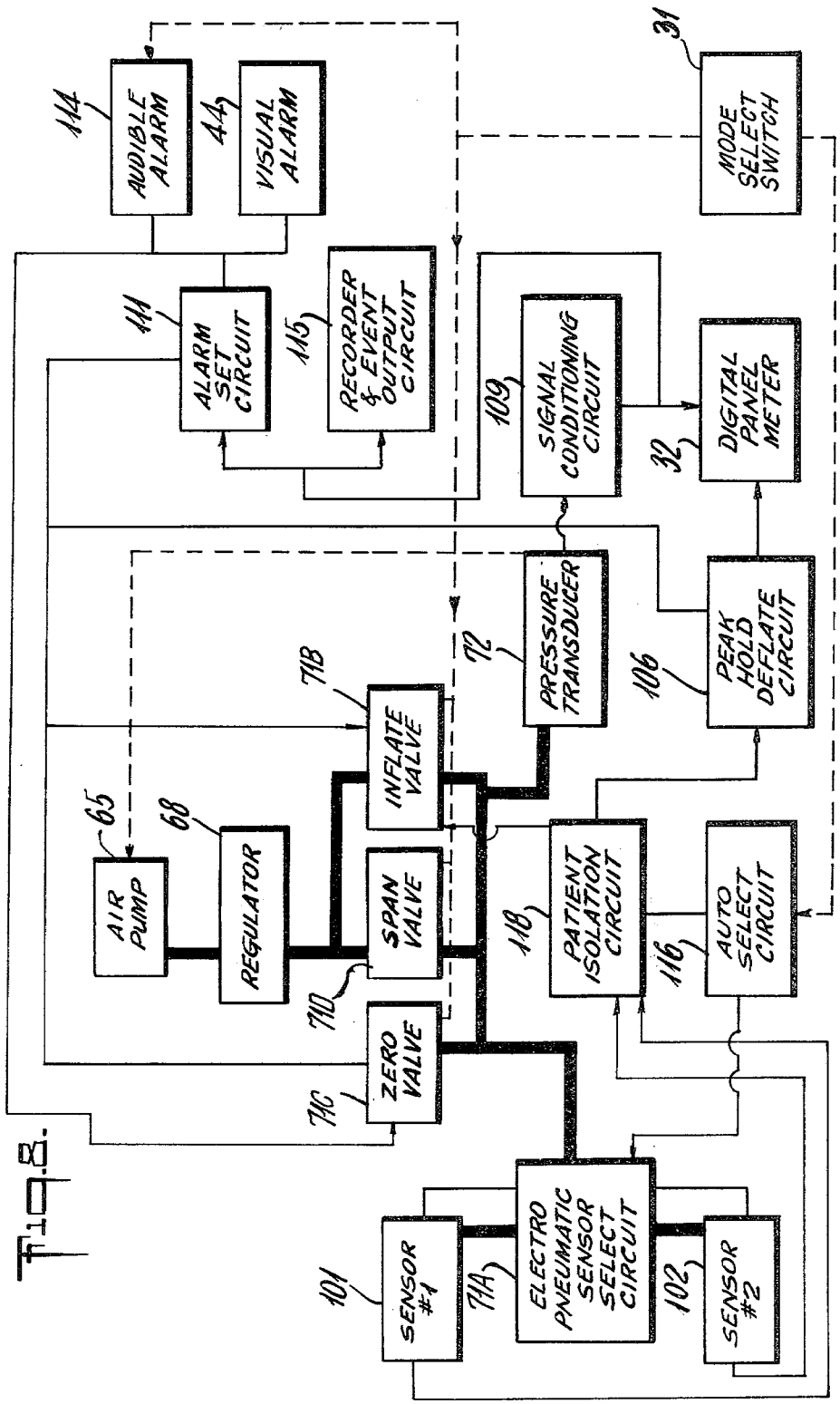

PRESSURE MONITORING SYSTEM FOR ELECTROFLUIDIC SENSING DEVICES

BACKGROUND OF THE INVENTION

The present invention relates to a pressure monitoring system, and, more particularly, concerns such a system for use with an electrofluidic device for sensing pressure, such as devices for monitoring intracranial pressure within the skull of a patient, and the like devices.

The accumulation of data relating to pressure measurements of various areas of a patient before, during and after surgery is heavily relied upon in order to provide a satisfactory understanding of the patient's tendencies. For example, the monitoring of intracranial pressure in patients who have undergone neurosurgery or who have hydrocephalic conditions provides the medical staff with information on the trends of pressure levels and serves as a clear indication should the intracranial pressure rise to levels which could cause brain damage or worse. One technique for monitoring pressure which is particularly amenable to procedures of intracranial pressure monitoring includes the employment of a device known as a Numoto switch. The Numoto switch is a pressure-actuated device generally constructed of a thin, flat flexible envelope, and a pair of electrodes inside the envelope usually attached to the flat walls of the envelope and movable so that, depending upon the pressure inside the envelope, they may either contact each other or move away from each other. An electrical lead is connected to each electrode to provide an electrical connection therefor. A flexible air tube is generally connected to the envelope both for providing air, or other fluids, into the envelope and for enclosing the electrical leads which extend therethrough. By an appropriate connection, the Numoto switch is connected to a fluid source for providing fluid into the envelope and also for indicating the pressure level of the supplied fluid.

This Numoto-type switch and one application and technique of using the same is described in U.S. Pat. No. 3,649,948. In the procedure explained in this patent, the switch is implanted within the skull of the patient in order to be in proper position for detecting intracranial pressure. As long as this intracranial pressure applied to the envelope of the switch exceeds the air pressure within the switch, the two electrodes will be maintained in contact with each other, serving as a closed electrical switch. Through the electrical leads, this switch is indicated on an ohmmeter as being closed; this then alerts the operator that the applied intracranial pressure exceeds the pressure inside the switch envelope. To detect this applied pressure level, the operator, relying upon fluid inside a reservoir of a manometer, slowly injects the fluid through the flexible tubing into the switch envelope. When the pressure inside the envelope just exceeds the intracranial pressure, the walls of the envelope are forced apart, whereupon the electrodes separate, and electrical contact is broken. Once again, through the electrical leads, the ohmmeter provides an indication that electrical contact has been broken inasmuch as the ohmmeter indicator should now read zero. At this point, the operator reads the pressure level of the injected fluid on the manometer. The balance of applied pressure and fluid inside the envelope is maintained by the operator alternately withdrawing and injecting fluid from the reservoir into the envelope, causing the electrical contacts to close and open with this alternating procedure.

It can be seen that utilization of the Numoto switch for monitoring pressure, and particularly intracranial pressure, is a reliable device inasmuch as only the straightforward balance of internal pressure inside the switch envelope with applied external pressure is required. However, the fluid providing system, the electrical monitoring approach and the pressure level reading element of the total system described in U.S. Pat. No. 3,649,948, while apparently workable in many respects, is deficient in others. Particularly, the fluid injection system to alternately balance the internal pressure with the applied external pressure is apparently performed manually by the operator; this, of course, is cumbersome for many applications of this type switch, and needs an operator for its performance. In addition, the operator must first observe the detection needle on the ohmmeter in order to have knowledge when the electrodes are either in contact or out of contact with each other, while at the same time trying to observe the manometer for the pressure level reading. Moreover, the manometer is merely a pressure gauge which oftentimes does not provide the accuracy which is necessary in situations such as the monitoring of intracranial pressure levels.

With these deficiencies in mind, it can be seen that there is room for improvement in many aspects of a pressure monitoring system which particularly uses an electrofluidic pressure sensing device, such as the Numoto switch. In particular, more reliance on automation is desirable inasmuch as this would substantially reduce the operator's time and attention for the mechanical aspects of operating such a system. Furthermore, clear, accurate readings, preferably digitalized, would provide a significant aid to the medical staff in assessing the pressure level readings. Various safety features, including an effective alarm system, are also desirable to provide an indication when dangerously high levels of pressure are being encountered; these safety features would also desirably be activated automatically so that constant attention to the display meter would be unnecessary. Other areas of improvement may also be incorporated in a pressure monitoring system of this device as desired by the operator.

SUMMARY OF THE INVENTION

A pressure monitoring system for use with an electrofluidic device for sensing pressure comprises means for supplying fluid to the electrofluidic sensing device. The system includes means for controlling the supply of fluid to the sensing device responsive to the external pressure level applied to the sensing device, and to cyclically cause the supplied pressure to vent at each occurrence when the pressure of supplied fluid inside the sensing device is substantially equal to the applied external pressure, whereupon the fluid supplied to the device is started again in cyclic fashion. Means for detecting the pressure level of the supplied fluid is provided, and there is means for displaying the analogous detected pressure level during supply of the fluid.

In the preferred embodiment of the present invention, an electrical switching circuit controls the supply of fluid to the sensing device. The means for detecting the pressure level of the supplied fluid is a transducer adapted to convert the detected pressure level into an analog voltage signal. In conjunction with this transducer, the display means is a digital display meter which receives the analog voltage signal from the transducer and numerically displays a numerical voltage reading corresponding to the maximum detected pressure level of the supplied fluid for a short period of time commencing at each instant when the supply of fluid to the sensing device is terminated. This preferred embodiment, moreover, is designed for use with a plurality of electrofluidic sensing devices and includes a selection mechanism having positions thereon to correspond with the individual sensing devices to which fluid is supplied. In this selection mechanism, there is included an automatic position which, when selected, enables sequential operation and monitoring of each individual sensing device for short periods of time. Furthermore, the preferred embodiment of this invention includes a pre-selectable maximum pressure level for the supplied fluid associated with the switching circuit so that when the level of the supplied fluid exceeds the pre-selected level, the supply of fluid to the sensing device is vented and an alarm activated. When the alarm is activated, operable reset must be provided for re-instituting the operation of the monitoring system.

In accordance with the principles of the present invention, an automated pressure monitoring system is provided which overcomes the deficiencies noted above with respect to prior art systems for use with electrofluidic pressure sensing devices. It is appreciated that the automatic detection of a pressure balance between applied pressure to the sensing device and an internally generated pressure is not only time saving, but lends accuracy to the system. Rapid results and readings are produced by the system of the present invntion, while the digital display meter provides an actual numerical reading rather than the capillary height reading associated with a pressure manometer. In addition, the accuracy of the system is enhanced as the balance of internally generated pressure to an externally-applied pressure is independent of external temperature which could cause inaccuracies if not accounted for. By providing an automated pressure monitoring system, another advantage and feature is an alarm system which serves to indicate to the operator that a pre-selected pressure level has been exceeded; the present system can be made to cease operation of supplying fluid inside the sensing device once the pre-selected pressure level has been exceeded and the alarm activated. As a further advantage, the present pressure monitoring system allows more than one sensing device to be monitored, since many times the surgeon may rely upon more than one sensing device to accumulate the data which he requires either during or after surgery. With this feature, the automated pressure monitor can scan and control each pressure sensing device in sequence. It is appreciated that scanning too many pressure sensing devices can be counterproductive inasmuch as it may take too long for the system to return to the first device; with this in mind, the present invention preferably has the capability for monitoring and controlling only two pressure sensing devices. The venting feature of the system provides for the release of supplied fluid from the sensing device a allow the maximum internally generated pressure level to be detected and monitored. Other advantages of the present monitoring system are offered as well, such as a feature to change the scale of the digital display meter to read in different units, such as one reading of pressure in millimeters of mercury (mm/Hg) or to read in centimeters of water (cm/H2O); internal calibration elements provide this range control feature.

BRIEF DESCRIPTION OF THE DRAWINGS

FIG. 1 is a perspective view of the preferred pressure monitoring system of the present invention shown with one embodiment of an electrofluidic intracranial pressure sensing device;

FIG. 2 is a front elevational view of the front panel of the preferred pressure monitoring system of FIG. 1;

FIG. 3 is a rear elevational view illustrating the rear panel of the preferred pressure monitoring system of FIG. 1;

FIG. 4 is a schematic diagram illustrating the major fluidic components of the present monitoring system as packaged inside the housing;

FIG. 5 is an enlarged cross-sectional view taken along line 5—5 of FIG. 1 illustrating the pressure sensing device in the closed position;

FIG. 6 is an enlarged cross-sectional view similar to the view of FIG. 5, but with the switch in the open position;

FIG. 7 is a plot of recorded output of the digital display meter illustrating the detected readings in pressure units as a function of time;

FIG. 8 is a block diagram schematically illustrating the functioning of the preferred pressure monitoring system.

DETAILED DESCRIPTION

Figure 9:
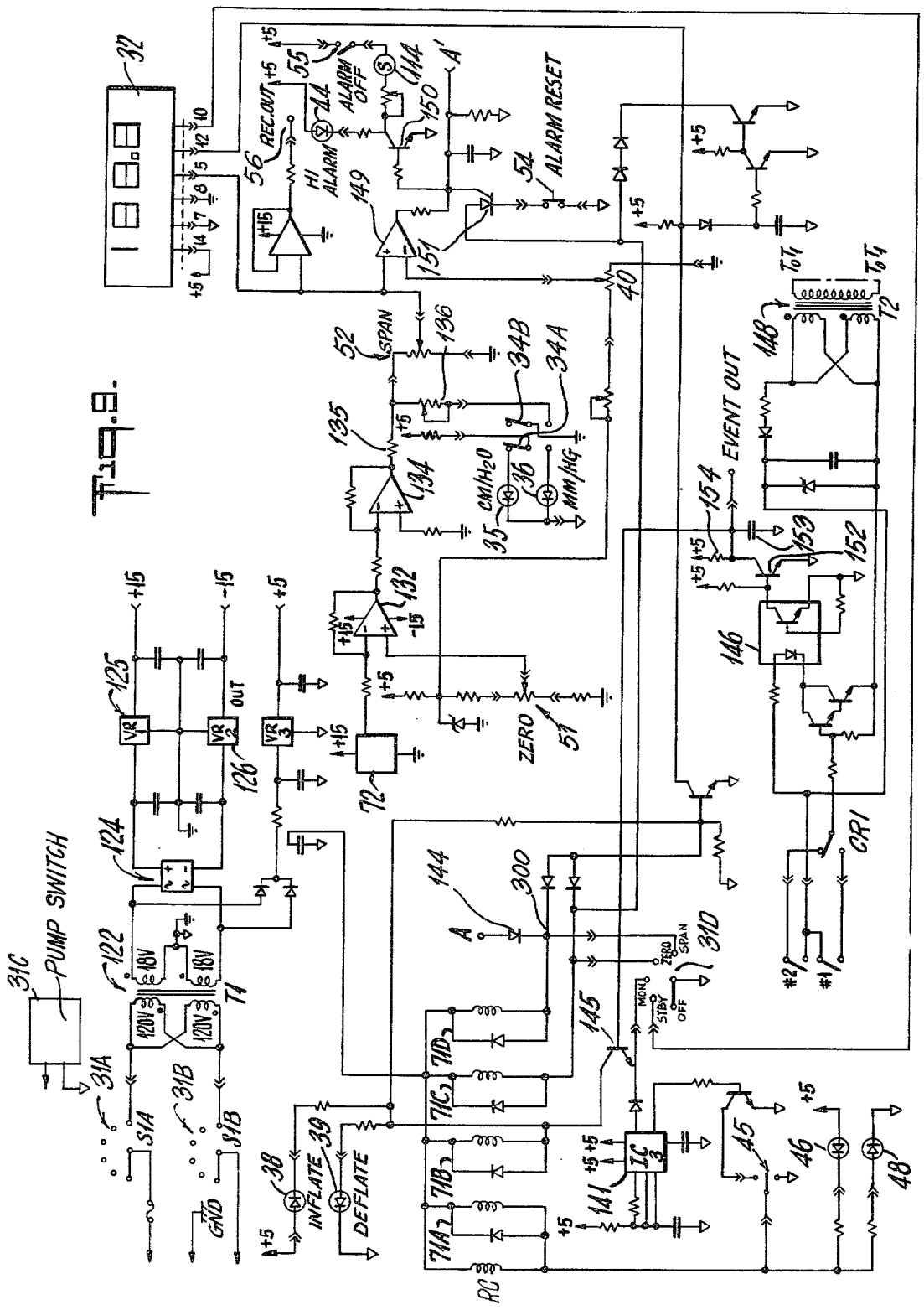
FIG. 9 is an electrical circuit diagram illustrating the preferred components of one working embodiment of the present invention.

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a pressure monitoring system 20 particularly useful with an electrofluidic device for sensing pressure. One such pressure sensing device 22 is shown connected to pressure monitor 20 by means of flexible tubing 24 which extends between pressure device 22 and an appropriate connection site on the rear panel of the pressure monitor as hereinafter described. The pressure monitoring system is essentially enclosed in a housing 25, preferably made from a lightweight material such as molded high-impact plastic. Housing 25 is compact and box-shaped, and includes a handle 26 which may be rotated around pivot pins 28 on the lateral sides of the housing to be used as a front stand or as a handle for carrying the system. The control and main features of this pressure monitoring system are found on a front panel 29 and a rear panel 30.

Turning now to FIG. 2 in conjunction with FIG. 1, front panel 29 is illustrated in greater detail. Main control switch 31 includes at least five positions for the particular device being described: "OFF," "STBY," "MONITOR," "ZERO," and "SPAN." In the "OFF" position, all functions of the system are inoperative. In "STBY," power is supplied to the solid state transducer inside the housing for warmup. Approximately five minutes of operation are allowed in this "STBY" mode to stabilize the output of the transducer and to minimize drift of the digital signal in the system. The "MONITOR" position is used after the "STBY" position, and it is in this position that the system is ready for full automatic operation. "MONITOR" is used in conjunction with one pressure sensing device at a time. When this position has been selected, the pressure supply pump inside the housing will immediately operate and the digital display 32 will light, indicating the bias voltage on the solid state transducer. At this time, the reading should be 00.0. If not, digital display meter 32 is adjusted by turning main control switch to "ZERO." In this position, the transducer is opened to atmosphere so that a zero reading adjustment can be performed. The "SPAN" position is provided to provide a full scale reading of digital display 32; for instance, the scale in millimeters of mercury (mm/Hg) is generally 0 to 100.0. If th gain of the digital display has changed, the display can be adjusted so that the reading is 100.0 with the system set on "SPAN" position.

Digital display meter 32 is designed to display a numerical reading of pressure supplied by the pressure monitoring system to pressure sensing device 22. In this embodiment, the reading on display meter 32 is a numerical voltage substantially equivalent to the detected pressure level of the fluid supplied to the inside of the pressure sensing device 22. A scale range switch 34, essentially a two position toggle switch, is utilized to permit the meter to display voltages in two different scale ranges; either centimeters of water or millimeters of mercury. A scale light indicator 35 is provided to indicate that the readings are in centimeters of water, while a scale light indicator 36 informs the operator that the display readings are in millimeters of mercury. When the scale range of the digital meter is set in the millimeters of mercury position, the scale is approximately 100.0, whereas in the centimeters of water position, the digital display reads about 135.7, these values being derived from the internal calibration of this system. Two operation indicator lights are provided, an inflation indicator 38 which indicates that fluid from the pressure monitor is being supplied to the sensing device since the switch inside the sensing device is closed; a deflation indicator light 39 is provided to indicate that the contact switch inside the pressure sensing device is open and that the mode of operation is in deflation. A digital pressure alarm set 40 is provided so that the maximum pressure level for supplied fluid to the pressure sensing device may be pre-selected. Generally speaking, the surgeon or other operator familiar with the procedure at hand, either by experience or having data available from previous testing, digitally sets the alarm level to a value which indicates that a maximum safe pressure level has been reached. Pressure alarm set 40 includes a two position adjustable digital potentiometer 41 and 42 which provides a range for the various values to be set. This potentiometer is calibrated on the same scale to correspond to whichever scale is selected for digital display meter 32. When the internal pressure generated by the pressure monitoring system and supplied to the pressure sensing device exceeds the set alarm pressure, an alarm indicator 44 lights on the front panel. This alarm light serves as a safety precaution and informs the operator that the internally generated pressure (balancing the applied external pressure to the pressure sensing device) has exceeded the preselected alarm level.

A sensing device selection switch 45 includes three positions thereon, namely one, two and "AUTO." On positions one or two, only one pressure sensing device will be monitored corresponding to the position selected. However, in the "AUTO" position, two pressure sensing devices will be monitored and controlled sequentially. In operation in the "AUTO" position, the pressure monitoring system will operate only with respect to, for example, the first pressure sensing device whereupon sensing device operation light 46 will be on. After scanning this pressure sensing device for approximately 20 seconds, the pressure monitor sequentially turns to the next pressure sensing device and starts monitoring and controlling it for about the same period of time, whereupon sensing device operation light 48 is lit. These lights inform the operator which of the pressure sensing devices is being monitored. Thus, in the "AUTO" selection position, the monitoring system alternately monitors and control two pressure sensing devices. It can be appreciated that the system can be designed to control many more than two devices, with the same sequential operation in mind. For practical purposes, the present invention is concerned only with a two position device with the automatic feature included. Accordingly, the cyclic operation is merely an alternating operation since only two pressure sensing devices are being monitored.

Turning now to FIG. 3 wherein rear panel 30 of the pressure monitoring system is illustrated, it can be seen that there is a provision for making a connection for two pressure sensing devices. These provisions are generally female sockets 50 which are designated to provide an electrofluidic connection; i.e. it is through this connection that both an electrical connection and a fluidic connection, such as for air or other fluids, is provided. Various type electrofluidic connectors may be employed, preferably with a female socket mounted directly in rear panel 30 of the pressure monitoring system; one typical electrofluidic junction is described in U.S. Pat. No. 3,649,948. On this rear panel is a zero adjustment 51 which is used in conjunction with the "ZERO" position on the main control switch on the front panel. If the digital display meter does not read zero when the main control switch is in that position, a zero control potentiometer 51 is provided to make the proper adjustment; a clockwise turn will increase the reading, whereas a counterclockwise turn will decrease the reading until proper balance is achieved. Along the same lines, a span gain control potentiometer 52 is provided for use in conjunction with the "SPAN" position on the main control switch. For example, on the millimeters of mercury scale, the span reading should read 100.0; if not, the span gain control potentiometer 52 may be adjusted to provide the correct reading. A turntable, adjustable control screw 53 is provided to allow variations in the rate fluid supplied to the sensing device; slower or faster rates may be desirable depending upon the specific application of the sensing device. An alarm reset button 54 is associated with the alarm indicator light 44 on the front panel and also in conjunction with the maximum alarm level 40 set by the operator beforehand. When alarm light 44 is activated due to the excessive pressure levels generated inside the pressure sensing device, the supplied fluid to the sensing device is vented to atmosphere as a safety precaution. When this occurs, the system will not operate until alarm reset button 54 is depressed. At this time, alarm indicator light 44 will go off, and fluid supply to the pressure sensing device can continue. In addition to the visual indicator alarm on the front panel, a two position toggle switch 55 provides an optional audible indicator feature. Thus, if the operator of this system would prefer to have an audible alarm signal when the pre-selected pressure level has been reached, the switch may be turned to the "ON" position. In this embodiment being described, there will be no audible indicator unless the operator elects to place this switch in the "ON" position. Reset button 54 will control both visual and audible indicator alarms so that, once they are activated, depression of the reset button will turn both of them off and allow the system to once again become operational.

Two phone-type jacks are provided, one to make an attachment for a recorder output 56, the other for an event output 58. Recorder output 56 is designed to provide a direct output signal corresponding to the voltage signal corresponding to the voltage reading of the display meter so that the monitored pressure levels can be plotted as a function of time. Event output 58 is designed to provide a DC signal each time the electrodes make or break contact so that the inflate/deflate mode can be ascertained. A fuse 59 is provided for safety purposes while a detachable hospital grade AC cord and plug 60 is provided to make the proper connection to energize the system.

In FIG. 4, the major internal fluidic components of this pressure monitoring system are schematically diagrammed so that the correlation between these components, the control features on the front and rear panels, and the functioning of the pressure monitoring system previously described can be understood. An air pump 65 is mounted within the housing for the purpose of supplying air to the electrofluidic pressure sensing device connected to the monitoring system. This pump is preferably electrically operated, and in conjunction with the electrical switching circuit (as hereinafter more fully described) is designed to supply the air controllably to the pressure sensing device only when the pressure inside the sensing device is less than the external pressure applied to the sensing device, such as during the monitoring of intracranial pressure levels. Most of the control circuitry is found on a printed circuit card 66, shown in phantom lines in FIG. 4. An air valve regulator 68 is connected to air pump 65 through tubing 69 and serves to control the rate of air flow from the pump into the inside of the pressure sensing device. For example, with the pump operating, air is regulated to flow into the sensing device through variable flow restrictor 73 so that the rate of air flow can be controlled by control screw 53 on the rear panel. With this controllable, variable restrictor the fill rate may be varied, for example, from 4 mm/Hg per second to 16 mm/Hg per second, or other rates as desirable and compatible with the flow restrictor. In addition, air regulator 68 is adapted to assist in stabilizing the selected air flow rate when the pump is operating and to provide the capability of venting the supplied air to atmospheric pressure level when the operation of the pump terminates during its cyclic operation. A filter 70 is provided in the tubing system so that particulate matter may be filtered out of the air being pumped into the sensing device.

From air regulator 68, the air flow is carried to a series of four solenoids 71 A, B, C and D which operate in conjunction with a transducer 72 (actually mounted on printed circuit card 66) for the purpose of detecting and measuring the levels of pressure being supplied from the air pump to the pressure sensing device, and then convert the measured pressure into an analog voltage signal. Pressure transducer 72 is preferably a pressure sensitive solid state transducer capable of producing an output voltage analogous to the level of pressure applied to the transducer. These transducers are well known and may be selected according to the choice of the designer in order to satisfactorily perform the functions of this pressure monitoring system. Manifold 75 is an open chamber into which tubing 69 connects to provide interconnection for the fluid flow through solenoids 71 A, B, C and D.

On rear panel 30 of the monitoring system, each female electrofluidic socket 50 is shown connected by tubing 69 to solenoids 71 A, B, C and D. One or more electrofluidic pressure sensing device is connected to female sockets 50 and on into the sensing device. Air is supplied to the sensing device until a substantial balance is achieved between internally supplied pressure and externally applied pressure on the sensing device. Inasmuch as the supplied air is plumbed through the various output solenoids and the transducer, the pressure level of the supplied air can be detected by the transducer and converted into an electrical analog signal for display on the digital meter. Of course, while two female sockets are shown for the purpose of allowing two sensing devices to be monitored, it is appreciated that only one device is controlled and monitored at one time with the fluidic elements illustrated. However, as explained above, with regard to FIG. 2, in the "AUTO" switching mode, the monitoring system is programmed to alternately scan two pressure sensing devices.

Referring now to FIGS. 5, 6 and 7, the general operation of the present pressure monitoring system in conjunction with an intracranial pressure sensing device will be described. Pressure sensing device 22 generally includes a fluid inflatable housing 80 with a pair of contact electrodes 81 and 82 inside the housing, with an electrical lead 84 and 85 connected to each electrode. Flexible tubing 24 is connected to housing 80 to provide fluid flow into the housing, and also to serve as an enclosure through which electrical leads 84 and 85 extend so that the proper connection can be made to the pressure monitoring system, preferably through an appropriate electrofluidic connector. Utilizing such a pressure sensing device, for example, as an intracranial pressure monitor, the housing is generally disc-shaped, and is implanted within the skull of a patient such as described in U.S. Pat. No. 3,649,948. The intracranial pressure maintains electrodes 81 and 82 in contact with each other inasmuch as the pressure applied externally to the housing equals or exceeds the internal pressure within the housing. With the pressure monitoring system energized, these contacting electrodes serve as a closed switch sending a signal to the switching circuit to cause fluid to be supplied through tubing 24 into housing 80. This pressure level increase inside the housing is graphically illustrated by the recorded output of the pressure monitoring system in FIG. 7. The increasing slope designated by numeral 86 at any given time indicates that the pressure level inside the housing is increasing; the preferred pressure monitoring system provides an inflation rate of approximately 8 millimeters mercury per second (12 centimeters of water per second), controlled by a pre-set through adjustment screw 53 on the rear panel. Once the pressure of the supplied fluid inside housing 80 is substantially equal to the applied external pressure against the intracranial device, the housing walls separate, thereby carrying with them electrodes 81 and 82; this condition is illustrated in FIG. 6, such that the separated electrodes serve as an open switch in the electrical circuitry. At this occurrence, the electrical switching controls in the system terminate the supply of fluid to the sensing device and cause the supplied fluid to be vented to atmospheric levels so that the pressure inside the housing can return again to the reference atmospheric pressure condition. This occurrence is also seen by once again alluding to FIG. 7 where the peak 88 of the plotted trace indicates the calibrated intracranial pressure detected at the moment electrodes 81 and 82 separate and the supplied fluid is vented. Immediately following peak 88, the plotted trace is illustrated in a decresing slope 89 which indicates that the supplied fluid has been vented to atmosphere and the level of pressure inside the housing will return to atmospheric levels. The rate of return to atmospheric pressure levels inside the housing will normally be greater than the metered inflation rate of the sensor as the sensor is vented to atmosphere through the zero valve. After each such venting, and as long as external pressure is still being applied to the sensing device, electrodes 81 and 82 will once again come in contact with each other thereby causing the entire cycle to repeat itself so that, as seen on the plot in FIG. 7, a series of peaks 88 will form a locus line indicating the maximum detected pressure level of the fluid supplied to the sensing device. The plot of FIG. 7 indicates that, for example, the maximum calibrated output of the system is achieved approximately five to six times per minute. It should be pointed out when referring to FIG. 7, that this recorded output is only for one pressure sensing device; if two devices were being utilized and the system was set on the "AUTO" mode, one device would be scanned for approximately twenty seconds so that maximum calibrated pressure readings would take place about two times; then, the operation would sequentially move to the next sensing device again for another twenty second scan time allotted.

While FIG. 7 traces the measurement of the internally generated pressure as a function of time for recording purposes, during the operation of this system digital display meter 32 would normally provide an instantaneous, current numerical reading of the pressure levels of supplied fluid. It can be appreciated that the numerical values will be changing rather rapidly during the increase of pressure into the housing of the sensing device. Accordingly, digital display meter 32 is designed to maintain the numerical reading at the maximum level achieved when electrodes 81 and 82 become separated; this numerical reading is held for a period of about five seconds at each instant when the supply of fluid to the sensing device is terminated or when the electrodes break contact. Thus, an observer of the digital meter will be able to read a fixed value on the meter corresponding to the maximum pressure level detected inside the housing which corresponds to the applied external pressure sensed by the sensing device. In other words, even though the fluid is being vented from the sensing device at this time, the digital display is designed to hold the maximum reading for a sufficiently generous period of time for the observer to take note or even record such a reading if it is not being plotted by means of the recorded output.

Turning now to FIG. 8, the functioning of this pressure monitoring system is illustrated in a block diagram of the functioning components. Sensor Number One 101 and sensor Number Two 102 represent the two electrofluidic pressure sensing devices which the present monitoring system is capable of monitoring, substantially as described above in conjunction with FIGS. 5 and 6. When the electrodes inside the sensing device are in electrical contact, air is caused to enter either sensor 101 or sensor 102 by way of the inflate valve 71B and the electrofluidic select circuit 71A. Air is applied to sensor 101 or 102 until the electrodes therein break contact as a result of the internally supplied pressure being substantially equivalent to the applied pressure external to the respective sensing device. Air is supplied by means of air pump 65 and controlled by regulator 68 as described previously. During supply of air to the sensing device, pressure transducer 72 is measuring and detecting the pressure levels of the supplied air so that the detected pressure level can be converted into an electrical analog signal. When the electrodes inside a sensing device break electrical contact, the peak, hold and deflate circuit 106 locks the digital meter 32 at the pressure level which pressure transducer 72 has detected at the instant the electrodes in the sensing device break contact. This represents the maximum pressure attained inside the sensing device which corresponds to the maximum applied pressure external to the sensing device. This reading is maintained on the digital meter for approximately 5 seconds. In the meantime, the peak, hold and deflate circuit 106 opens the zero valve 71C thereby venting the air inside the sensing device to atmospheric levels. As the pressure inside the sensing device is reduced, the electrodes therein will again make electrical contact. Once contact is made, there is a three second delay before inflate valve 71B controls the air from the air pump to supply air to the appropriate sensor 101 or 102 to sequentially start the cycle over again.

A conditioning circuit 109 provides the zero and full scale pressure adjustments for the digital meter 32. Zero is adjusted by setting the main control switch 31 on the front panel in the "ZERO" position, which opens zero valve 71C to atmosphere. The full-scale air span is adjusted by placing main control switch 31 into the "SPAN" position. Air is regulated to the full scale reading of the digital display meter, for example, 100 millimeters of mercury, precisely by the air regulator 68 and then is supplied to the span valve 71D or the inflate valve 71B, depending on whether the main control switch is on the "SPAN" or "MONITOR" position, respectively. This full scale regulation serves as an internal reference providing a self-contained feature for full calibration of the monitoring system.

An alarm set circuit 111 compares the pressure set on the front panel by way of the two position digital potentiometer 41 and 42 with the pressure being displayed on digital meter 32. When the displayed pressure, determined by way of pressure transducer 72, exceeds the preset point on the front panel, alarm set circuit 111 will cause alarm indicator 44, preferably a light-emitting diode, to light thereby providing a visual alarm on the front panel during operation. If the operator has activated switch 55 for the optional audible indicator feature on the rear panel, alarm circuit 111 will also cause an audible alarm 114 in the form of a 1,000 hertz tone. A recorder and event output circuit 115 buffers the pressure signal for connection to an external chart recorder, the connection being made through phono-jacks 56 and 58 on the rear panel of the monitoring system. As noted earlier, the event recorder output is provided for examining the peak reading on the plotted chart.

Auto select circuit 105 is provided in conjunction with selection switch 45 on the front panel to select the monitoring of either sensor 101, sensor 102 or the automatic scan mode for sequentially and alternately monitoring both pressure sensing devices. A patient isolation circuit 118 isolates the patient from electrical ground for purposes of safety.

In FIG. 9, the electrical circuit diagram illustrates the preferred combination of components to provide the capabilities and functions as described above with reference to FIG. 8. Most of the components illustrated in FIG. 9 are located on the printed circuit board described in conjunction with FIG. 4. Switch 31A, 31B, 31C and 31D denote the multi-position control switch 31 on the front panel of the monitoring system. Line voltage enters through transformer 122 where it is reduced to 18 volts AC. The full wave rectifier 124 and the voltage regulators 125 and 126 generate +15 volts and −15 volts supply voltage for the system. The solid state pressure transducer 72 may be a stock component such as National Semiconductor part no. LX1601G, and is powered from one leg of the +15 volt power supply.

This transducer is plumbed through various output solenoids 71A, 71B, 71C and 71D providing a fluidic connection between transducer, pump and one of the pressure sensing devices 1 or 2. The output voltage of the transducer analog to the pressure input is then fed into amplifier 132. The zero adjust 51 works in conjunction with amplifier 132, providing the user with a method of nulling the zero offset. From here the signal is fed into amplifier 134. The output of this amplifier 134 is scaled by the span control 52, providing the user with a method of calibrating the devices span range. The output of amplifier 134 is modified by switch 34 to provide a second calibrated measuring unit. With switch 34 in position shown, section 34A provides a signal to turn on light emitting diode 35 indicating the unit is calibrated for measuring centimeters of water. With switch in other position section 34A provides a signal to light emitting diode 36, indicating the unit is calibrated for measuring millimeters of mercury. Also in this position section 34B modifies the output of amplifier 134 by the resistive divider accomplished by 135, 136. These zero, span and measuring unit features are represented by signal conditioning circuit 109 of FIG. 8.

The output of second stage amplifier 134 is fed into pin No. 5 on the digital panel meter 32, which is located on the front panel of the monitoring system. This digital meter may be a standard item such as is presently available from Fairchild Instruments, part No. D.P.M. 300550. The adjusted amplified signal is displayed in millivolts equivalent to either millimeters of mercury or centimeters of water. The analog output signal is simultaneously fed into alarm set circuit 111 where a digital value of the millivolt signal can be set as a high limit for the system pressure. The millivolt signal arrives at the positive input of comparator 149. At this point, its value is compared to the value of the high alarm setting 40 located on front panel. If this millivolt signal exceeds the setting's value, the comparator will go positive setting silicone controlled rectifier 151 and thereby locking on transistor 150 due to the gate voltage of 151. Transistor 150 will turn on visual alarm 44 and audible alarm 114 warning the user of the high pressure condition. The S.C.R. 151 will open the zero valve 71C venting the sensor pressure as a safety precaution.

When switch 31D is set in the span position diode 144 causes a low voltage at point 300 in the circuit of FIG. 9. Point A above diode 144 is physically connected by an electrically conductive wire to point A' shown below audible alarm 114 putting a low voltage on the base/emitter circuit of transistor 150. Switch 55 (the toggle switch 55 on the rear panel) is provided to include an audible alarm 114 when the switch is closed and when the high pre-level is exceeded. Alarm reset 54 allows the audible alarm to be turned off once the system is tripped by the high signal, and also to reset the system for operation and control of the pressure monitoring devices.

The automatic scanning features of the present system are controlled by means of the integrated circuit device 141, in conjunction with switches 31D and 45. This integrated circuit is available from Signetics Corporation, part No. NE555V, and performs the function indicated by manual/auto sensor select circuit 105 of FIG. 8. The peak hold function is accomplished by the circuit including transistor 152, capacitor 153, and resistor 154. The digital meter will hold its reading whenever the sensor contactors are open. When the sensor contacts close transistor 152 shuts off. However, the circuit creates a time lag, giving the impression the contacts are still open. This lag is approximately 5 seconds. Switch 31D controls the various positions provided to the main control switch 31 on the front panel and is represented by mode select switch 31 in FIG. 8. Solenoids 71B, 71C, 71D are provided to control the pressure flow in the MONITOR, ZERO and SPAN positions, respectively as selected by way of the main control switch 31. In the "AUTO" position switch 45 on the front panel is closed so that the alternating sequence for monitoring the two pressure sensing devices can become operational. Solenoid 71A is provided for this function, and light emitting diodes 46 and 48 indicate which sensing device is being monitored during the sequence. During the MONITOR mode, inflate valve 71B is operable to supply air to the sensing device. In addition, the inflate, deflate mode is also indicated by light emitting diodes 38 and 39, respectively, during the monitoring operation. The above described solenoids and associated switches form the electropneumatic sensor select circuit 105.

The event output circuit 115 receives a signal during the "MONITOR" mode of operation when switch 31B is closed across the "MONITOR" pole through transistor 145. In conjunction with phonojack 58 on the rear panel, this circuit is designed to provide a DC signal each time the electrodes inside one of the pressure sensing devices make or break contact. The approximate output level for such signal is 1.5 volts DC. On the other hand, the recorder output 115 is associated with both alarm set circuit 111 and digital panel meter 32 since the recorder output provides a direct output of the pressure in millivolts. The patient isolation circuit for isolating the patient from ground includes an optical coupler 146 and a low leakage transformer 148 and a relay RLI with its associated contacts RCI.

With regard to FIG. 9, only the major components in the electrical circuit have been described since many minor components serve to complement the aforementioned major components and are within the purview of one normally skilled in the art to select.

Thus, a pressure monitoring system for use with electrofluidic devices for sensing pressure is provided which automatically detects and displays the amount of pressure being externally applied to the sensing device. This monitoring system includes a high pressure alarm indicator to become activated when a pre-set level of pressure has been exceeded by the applied pressure to the sensing device.

What is claimed is:

1. A pressure monitoring system comprising:
   pump means for supplying fluid under pressure to a pump output;
   switching means for controlling the supply of fluid from said pump means output responsive to the pressure level being monitored said switching means adapted to terminate the supply of fluid from said output when the pressure of said supplied fluid to said output is substantially equal to the pressure being monitored and thereafter to vent said supplied fluid to atmospheric pressure levels so that said pressure being monitored exceeds the pressure level at said output, said switching means adapted to cyclically repeat said supply of fluid to said output after each such venting occurs;
   a measuring element to detect the pressure level of said supply fluid; and
   a display meter for numerically displaying the analogous maximum detected pressure level of said supply fluid for a short period of time commencing at each instant when said supply of fluid to said output is terminated,
   a second outlet for said pump;
   selection means having portions corresponding to each of said outlets for preselecting a position for which said switching means, said measuring element and said display meter are connected to one of said pump outputs at a time;
   said selection means including an automatic position, which, when selected, connects said pump means, switching means, said measuring element and said display meter to one output for a short period of time and sequentially connects the remaining output in the same fashion, and then reconnects the first output to cyclically repeat said sequence.

2. The system of claim 1 which further includes means associated with said switching means for selecting a predetermined, alarm sensitive maximum pressure level for said supplied fluid means responsive to any pressure level of said supplied fluid in excess of said maximum predetermined level, for venting the supplied fluid and for activating an alarm.

3. The system of claim 1 wherein said pump means includes an air regulator adapted to control the rate of air flow when said pump is operating and to provide the capability of venting the supplied air to atmosphere when the operation of the pump terminates during said cyclic operation.

4. The system of claim 3 which further includes means to controllably vary the air flow rate supplied from said pump means to said sensing device.

5. The system of claim 1 wherein said measuring element is a transducer which is adapted to detect the pressure level of fluid supplied to said device and to convert the same into an analog voltage signal.

6. The system of claim 5 wherein said display meter is a digital display device which receives the analog voltage signal from said transducer and displays a numerical voltage reading substantially equivalent to the detected pressure level of said supply fluid.

7. The system of claim 6 wherein said digital display device includes a range control switch which permits the display device to display values of voltage corresponding to different scale ranges of pressure readings depending upon the position of the switch.

8. The system of claim 1 which further includes recorder output means which provides a direct output signal corresponding to the voltage reading of said display meter whereby the monitored pressure levels can be plotted as a function of time.

9. A pressure monitoring system for use with a plurality of electrofluidic devices for sensing pressure comprising:
   a pump for supplying fluid under pressure to said sensing devices;
   an electrical switching circuit for controlling the supply of fluid to each sensing device responsive to the pressure level being monitored and adapted to terminate the supply of fluid to said device when the pressure of said supplied fluid is substantially equal to the pressure being monitored, and thereafter to vent said supplied fluid to atmospheric pressure levels so that said pressure being monitored exceeds the pressure level of fluid inside said device, and further adapted to cyclically repeat said supply of fluid to said device after each such venting occurs;
   a transducer for detecting the pressure level of said supplied fluid to a sensing device adapted to convert the detected pressure level into an analog voltage signal;
   a digital display meter which receives the analog voltage signal from said transducer and displays a numerical voltage reading corresponding to the maximum detected pressure level of said supplied fluid for a short period of time commencing at each instant when said supplied fluid to said sensing device is vented;
   a pre-selectable, alarm sensitive maximum pressure level for said supplied fluid associated with said switching circuit so that when the level of said supplied fluid exceeds said pre-selected level, the supply of fluid to said sensing device is vented and an alarm activated; and
   a selection mechanism having positions thereon to correspond with the individual sensing devices to which fluid is supplied for pre-selecting a position for said system to become operable so that only one device at a time is being monitored, said selection mechanism including an automatic position which, when selected, permits said selection mechanism to sequentially access each individual sensing device for short periods of time.

10. The system of claim 9 wherein said venting means prevents the cyclic operation of said fluid supply, said system further including operable reset means for reinstituting its operation.

11. The system of claim 10 wherein said alarm includes both a visual and an audible indicator, and wherein said alarm activating means is adapted to separately control said audible indicator and said visual indicator so that either may be utilized at the discretion of the operator.

12. In combination, a pressure monitoring system and an electrofluidic device for sensing pressure, said sensing device comprising a fluid inflatable housing, a pair of contact electrodes in said housing adapted to contact each other when pressure applied externally to said housing equals or exceeds the internal pressure within said housing, and adapted to operably move out of contact with each other when the internal pressure within the housing exceeds the externally applied pressure, said device including means to provide fluid flow to said housing and electrical lead means connected to said electrodes for monitoring electrode contact and noncontact, said sensing device connected to said pressure monitoring system through both said fluid flow means and said electrical lead means; said pressure monitoring system comprising:

means for supplying fluid to said sensing device;

electric switching means for automatically controlling the supply of fluid to said sensing device responsive to the external pressure level applied to said sensing device and to cyclically cause the supply pressure to vent at each occurrence when the level of supplied fluid inside said sensing device is substantially equal to said applied external pressure and then start said fluid supply to said device again in cyclic fashion;

means for detecting the pressure level of said supplied fluid; and means for displaying the analogous detected pressure level of said supplied fluid.

13. The combination of claim 12 wherein said system further includes means associated with said switching means for selecting a pre-selectable, alarm sensitive maximum pressure level for said supplied fluid means responsive to the pressure level of said supplied fluid in excess of, said maximum level, for venting the supply of fluid to said sensing device and for activating an alarm.

14. The combination of claim 12 wherein said detection means includes a transducer which is adapted to detect the pressure level of fluid supplied to said device and to convert the same into an analog voltage signal.

15. The combination of claim 12 wherein said system is adapted to monitor a plurality of electrofluidic devices and which includes selection means having positions to correspond with the individual sensing devices to which fluid is supplied so that only one sensing device at a time is to be monitored and controlled.

16. The combination of claim 15 wherein said selection means includes an automatic position when, when selected, permits said selection means to access said system with respect to an individual electrofluidic sensing device for a short period of time and sequentially access the remaining devices of said plurality in the same fashion, and then to return to the first of said devices to cyclically repeat said sequence.

* * * * *